US008546600B2

(12) United States Patent
Miller

(10) Patent No.: US 8,546,600 B2
(45) Date of Patent: Oct. 1, 2013

(54) SLURRY PROCESS FOR SYNTHESIS OF BISPHOSPHITES AND SITU USE THEREOF FOR PRODUCING BISPHOSPHITE

(75) Inventor: Glenn A. Miller, South Charleston, WV (US)

(73) Assignee: Dow Technology Investments LLC

( * ) Notice: Subject to any disclaimer, the term of this patent is extended or adjusted under 35 U.S.C. 154(b) by 173 days.

(21) Appl. No.: 13/122,975

(22) PCT Filed: Sep. 23, 2009

(86) PCT No.: PCT/US2009/057936
§ 371 (c)(1),
(2), (4) Date: Apr. 7, 2011

(87) PCT Pub. No.: WO2010/042313
PCT Pub. Date: Apr. 15, 2010

(65) Prior Publication Data
US 2011/0196166 A1   Aug. 11, 2011

Related U.S. Application Data

(60) Provisional application No. 61/103,717, filed on Oct. 8, 2008.

(51) Int. Cl.
*C07F 9/141* (2006.01)

(52) U.S. Cl.
USPC .......................................................... 558/90

(58) Field of Classification Search
None
See application file for complete search history.

(56) References Cited

U.S. PATENT DOCUMENTS

| | | | |
|---|---|---|---|
| 4,599,206 | A | 7/1986 | Billig et al. |
| 4,769,498 | A | 9/1988 | Billig et al. |
| 4,929,745 | A | 5/1990 | Keblys et al. |
| 5,235,113 | A | 8/1993 | Sato et al. |
| 5,391,799 | A | 2/1995 | Pastor et al. |
| 5,663,369 | A | 9/1997 | Kreutzer et al. |
| 5,688,986 | A | 11/1997 | Tam et al. |
| 6,031,120 | A | 2/2000 | Tam |
| 6,881,867 | B2 | 4/2005 | Ahlers et al. |
| 7,196,230 | B2 | 3/2007 | Peng et al. |
| 7,217,828 | B2 | 5/2007 | Selent et al. |
| 2006/0252969 | A1 | 11/2006 | Flores et al. |
| 2007/0112219 | A1 | 5/2007 | Ortmann et al. |
| 2007/0117995 | A1 | 5/2007 | Ortmann et al. |
| 2009/0247790 | A1 | 10/2009 | Miller |

FOREIGN PATENT DOCUMENTS

| WO | 2009120210 | 1/2009 |
|---|---|---|
| WO | 2009120529 | 1/2009 |

OTHER PUBLICATIONS

Su et al., Tetrahedron asymmetry, 14, 2003, 1865-1869.*
Buisman et al.; "Hydridorhodium diphosphite catalysts in the asymmetric hydroformylation of styrene", J. Chem. Soc. Dalton Trans., 1995, pp. 409-417.
Greene N et al.; "Asymmetric silylphophite esters: Synthesis and reactivity of (rac-O, O-binaphtholato) PosiR3 (R3=Ph3, t-BuMe2, Et3)", Synthetic Communications, vol. 23, No. 12, 1993, pp. 1651-1657.
Bredikhin A A et al.; "On the use of seven-membered phosphorous heterocycles based on 2,2"-dihydroxy-1, 1'-binaphthalene and 1, 4: 3, 6-dianhydro-D-mannitol in the 31P NMR analysis of the enantiomeric composition of chiral alcohols", Russian Chemical Bulletin, vol. 47, No. 3, 1998, pp. 411-416.
Buisman G J H et al.; "Rhodium catalysed asymmetric hydroformylation with chiral diphosphite ligands", Tetrahedron: Asymmetry, vol. 4 No. 7, 1993, pp. 1625-1634.
Beller M et al.; "Dual catalytic systems for consecutive isomerization-hydroformylation reactions", Chemistry—A European Journal, vol. 5, No. 4, 1999, pp. 1301-1305.
Van Rooy A et al.; "Bulky Diphophite-Modified Rhodium Catalysts: Hydroformylation and Characterization", Organometallics, vol. 15, No. 2, 1996, pp. 835-847.
Lot et al.; "New electron-deficient aminophosphonite-phosphite (ligands for asymmetric hydroformylation of styrene", Journal of Molecular Catalysis A: Chemical 164 (2000), pp. 125-130.
Korostyler et al.; "Chiral pyrophosphites-synthesis and application as ligands in Rh(I)-catalyzed asymmetric hydrogenation", Tetrahedron: Asymmetry, 14 (2003), pp. 1905-1909.
Cramer et al.; "Chiral Phosphites and phosphoramidites Based on the Tropane Skeleton and Their Application in Catalysis", Organometallics, vol. 25, 2006, pp. 2284-2291.
Barry et al.; "Triphenylphosphine-Tetrachloromethane Promoted Chlorination and Cyclodehydration of Simple Diols", Journal of Organic Chemistry, 1981, 46(16), pp. 3361-3364.
Gerrard et al.; "Basic Function of Oxygen in Certain Organic Compounds", Chemical Rev., 1959, 59, 1105-1123.
Ahmed et al.; "Significance of the Solubility of Hydrogen Halides in Liquid Compounds", Journal of Applied Chemistry, 1970, vol. 20, April, pp. 109-116.

* cited by examiner

*Primary Examiner* — Sun Jae Loewe
(74) *Attorney, Agent, or Firm* — Paul D. Hayhurst

(57) ABSTRACT

The present invention provides a step-wise process for preparation of a bisphosphite. In step (a) the process prepares a phosphoromonochloridite in high yield, by contacting phosphorus trichloride with an aromatic diol in a slurry under reaction conditions and in the presence of a second aromatic diol to produce a mixture comprising the phosphoromonochloridite, the second aromatic diol, and excess PCl3. The slurry comprises less than 5 mole percent of a nitrogen base, and the organic solvent is selected for its low hydrogen chloride solubility. After removing the excess PCl3, a nitrogen base is added to effect condensation of the phosphoromonochloridite with the second aromatic diol to yield the bisphosphite. The invention particularly provides a process for preparing 6,6'-(3,3',5,5'-tetra-tert-butylbiphenyl-2,2'-diyl)bis(oxy)didibenzo[d,f][1,3,2]dioxaphosphepine by the above route.

10 Claims, No Drawings

US 8,546,600 B2

SLURRY PROCESS FOR SYNTHESIS OF BISPHOSPHITES AND SITU USE THEREOF FOR PRODUCING BISPHOSPHITE

CROSS REFERENCE TO RELATED APPLICATIONS

This application is a 371 of PCT/US2009/057936 filed Sep. 23, 2009, which claims the benefit of U.S. Provisional Application Ser. No. 61/103,717, filed Oct. 8, 2008.

FIELD OF THE INVENTION

This invention relates generally to a process for preparation of phosphoromonochloridites, and to a process for in situ use of the phosphoromonochloridites for synthesis of organopolyphosphites.

BACKGROUND

Phosphites represent a diverse class of organic phosphorus compounds that are useful as ligands for homogeneous catalysis and as components of plasticizers, flame retardants, UV stabilizers, and antioxidants. Phosphites can be further classified as organomonophosphites and organopolyphosphites. Organopolyphosphites, particularly organobisphosphites, which are more commonly referred to simply as "bisphosphites," are particularly useful for certain homogeneous catalysis; for example, U.S. Pat. No. 4,769,498 generally relates to synthesis of organopolyphosphites, including bisphosphites, and use thereof as ligands in hydroformylation processes.

Organopolyphosphites are typically synthesized in stepwise processes using phosphoromonochloridites as intermediates; see, for example, U.S. Pat. Nos. 6,031,120, 5,663,369, and 4,769,498. A phosphoromonochloridite is typically synthesized in a condensation reaction by contacting phosphorus trichloride ($PCl_3$) with one molar equivalent of a di-alcohol or two molar equivalents of a mono-alcohol under reaction conditions dependent upon the reactivity of the starting alcohol and the resulting phosphoromonochloridite. For each molecule of a phosphoromonochloridite produced, the condensation reaction produces two molecules of hydrogen chloride (HCl). In order for the condensation reaction to achieve high, for example, greater than 90 percent, conversion of the alcohol, HCl needs be removed from the reaction solution.

One approach for HCl removal from the condensation reaction is to neutralize HCl using a nitrogen base in an amount stoichiometric to or in excess to the theoretical amount of HCl to be produced. See, for example, U.S. Pat. Nos. 5,235,113; 6,031,120, and 7,196,230, U.S patent application publication 2007/0112219 A1, and *Journal of Molecular Catalysis* A: Chemical 164 (2000) 125-130. When a nitrogen base is used, however, the resulting nitrogen base-HCl salt must be removed from the reaction mixture by a filtration procedure, which generates chloride and nitrogen-containing wastes that, in turn, increase cost.

Another approach for HCl removal from the $PCl_3$-alcohol condensation reaction involves heating a mixture of the alcohol and a large excess amount of the $PCl_3$ at a temperature sufficiently high to reflux $PCl_3$ (boiling point (bp): 74-78° C.), which drives off the HCl. In this approach, the nitrogen base is not needed or used. For example, U.S. Pat. No. 4,769,498 discloses a procedure for producing 1,1'-biphenyl-2,2'-diyl phosphoromonochloridite by refluxing a mixture of 2,2'-biphenol with 3.7 molar equivalents (2.7 equivalents in excess) of $PCl_3$. The phosphoromonochloridite product is disclosed to be isolated in 72 mole percent yield, based on moles of 2,2'-biphenol employed, by distillation under reduced pressure. Another procedure, as referenced in Korostyler et al., *Tetrahedron: Asymmetry*, 14 (2003) 1905-1909, and Cramer et al., *Organometallics*, Vol. 25, No. 9 (2006) 2284-2291, synthesizes 4-chlorodinaphtho[2,1-d:1',2'-f][1,3,2]dioxaphosphepine by heating a mixture of 1,1'-bi-2-naphthol and 11.5 molar equivalents of $PCl_3$ at 75-80° C. One undesirable feature of the aforementioned approach involves a need to remove and handle a large excess amount of $PCl_3$, which reacts exothermically with moisture and typically involves added safety considerations. It would be desirable to reduce the excess amount of $PCl_3$ to be used in the process.

When the $PCl_3$-alcohol condensation reaction uses a solid diol, yet another approach for HCl removal involves: a) dissolving the solid diol either in an aprotic polar organic solvent, preferably tetrahydrofuran (THF), or in a solvent mixture comprising an aprotic polar organic solvent, to produce a feed solution; and b) adding the feed solution slowly into a refluxing solution of $PCl_3$ dissolved in a hydrocarbon solvent, such as toluene. The refluxing is required to drive off the HCl as a gas from the reaction solution. The aprotic polar organic solvent, such as THF, is generally required to obtain a feed solution containing greater than 20 weight percent of the diol at ambient temperature, based on the weight of the feed solution, particularly if the diol has an unacceptable solubility in the hydrocarbon solvent. This process has been used commercially and is the subject of International Patent Application PCT/US08/58640, filed Mar. 28, 2008, for "ISOTHERMAL PROCESS FOR PHOSPHOROMONOCHLORIDITE SYNTHESIS," filed in the name of Union Carbide Chemicals and Plastics Technology LLC.

With reference to the aforementioned commercial process, hydrogen chloride is known to react with the preferred aprotic polar organic solvent, tetrahydrofuran, to produce 4-chlorobutanol; see, for example, Barry et al., *Journal of Organic Chemistry* (1981), 46 (16), 3361-4. Hydrogen chloride reacts with tetrahydrofuran more slowly at lower temperatures, if other conditions remain the same; however, operating at temperatures lower than about 98° C. can lead to accumulation of hydrogen chloride in the reaction solution in the form of THF-HCl complexes, which in turn can lead to an even higher rate of 4-chlorobutanol production. Disadvantageously, both $PCl_3$ and the phosphoromonochloridite react with 4-chlorobutanol to produce undesirable by-products. The phosphoromonochloridite is desirably used without further purification in the synthesis of organopolyphosphites. Formation of 4-chlorobutanol, however, during the phosphoromonochloridite condensation reaction not only reduces the yield of phosphoromonochloridite product, preferably, 1,1'-biphenyl-2,2'-diyl phosphoromonochloridite, but also complicates subsequent organopolyphosphite synthesis reactions.

As a further aspect of the aforementioned commercial process, any mixture of $PCl_3$ and THF recovered from the process typically is not reused due to the need to separate $PCl_3$ (bp: 74-78° C.) and THF (bp: 65-67° C.).

In view of the above, a need exists in the art for a more efficient process of producing a phosphoromonochloridite as well as a more efficient process of producing a bisphosphite.

SUMMARY OF THE INVENTION

In a first aspect, the present invention provides for a novel synthetic process for preparing a phosphoromonochloridite comprising contacting phosphorus trichloride ($PCl_3$) with an aromatic diol ("first aromatic diol") represented by Formula I:

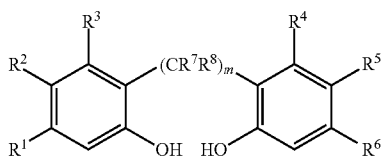

Formula I wherein:
  m is zero, 1 or 2;
  $R^1$, $R^2$, $R^3$, $R^4$, $R^5$, $R^6$, $R^7$ and $R^8$ are each independently selected from hydrogen, halogen, and $C_1$-$C_{10}$ substituted or unsubstituted hydrocarbyl moieties;
  and optionally, wherein $R^2$ is bonded to $R^3$ to form a substituted or unsubstituted hydrocarbylene moiety so as to form a 5- or 6-membered ring; and/or
  optionally wherein $R^4$ is bonded to $R^5$ to form a substituted or unsubstituted hydrocarbylene moiety so as to form a 5- or 6-membered ring.
in a slurry comprising a portion of the aromatic diol in solid form and comprising a solution phase comprising the remaining portion of the aromatic diol and an organic solvent, wherein the slurry comprises less than 5 mole percent of a nitrogen base, calculated on total moles of the aromatic diol, and the organic solvent has a low hydrogen chloride solubility; the contacting being conducted under reaction conditions sufficient to produce a phosphoromonochloridite represented by Formula II:

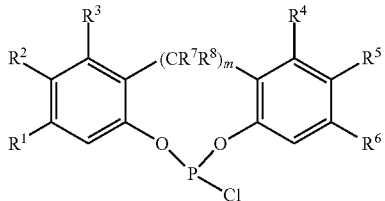

Formula II wherein m and $R^1$ through $R^8$ have the definitions given hereinabove.

In a second aspect, the present invention provides for a novel synthetic process for preparing a bisphosphite, the process comprising the steps of:
  (a) contacting phosphorus trichloride with a first aromatic diol represented by Formula I:

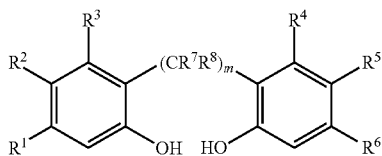

Formula I wherein:
  m is zero, 1 or 2;
  $R^1$, $R^2$, $R^3$, $R^4$, $R^5$, $R^6$, $R^7$ and $R^8$ are each independently selected from hydrogen, halogen, and $C_1$-$C_{10}$ substituted or unsubstituted hydrocarbyl moieties;
  and wherein optionally, $R^2$ is bonded to $R^3$ to form a substituted or unsubstituted hydrocarbylene moiety so as to form a 5- or 6-membered ring; and/or
  optionally, wherein $R^4$ is bonded to $R^5$ to form a substituted or unsubstituted hydrocarbylene moiety so as to form a 5- or 6-membered ring,
in the presence of a second aromatic diol represented by Formula III:

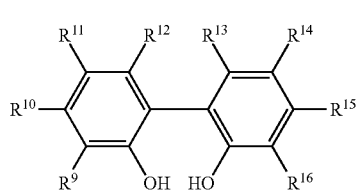

Formula III wherein:
  $R^9$ and $R^{16}$ are each independently selected from $C_1$-$C_{10}$ substituted or unsubstituted hydrocarbyl moieties,
  $R^{10}$ through $R^{15}$ are each independently selected from hydrogen, halogen, and $C_1$-$C_{10}$ substituted or unsubstituted hydrocarbyl moieties,
  and wherein optionally, $R^{11}$ is bonded to $R^{12}$ to form a substituted or unsubstituted hydrocarbylene moiety so as to form a 5- or 6-membered ring;
  and/or optionally, $R^{13}$ is bonded to $R^{14}$ to form a substituted or unsubstituted hydrocarbylene moiety so as to form a 5- or 6-membered ring;
  the contacting being conducted in a slurry comprising portions of the first and second aromatic diols in solid forms and comprising a solution phase comprising the remaining portions of the first and second aromatic diols and an organic solvent, wherein the slurry comprises less than 5 mole percent of a nitrogen base, calculated on total moles of the first aromatic diol, and the organic solvent has a low hydrogen chloride solubility; the contacting being conducted under reaction conditions sufficient to produce a first mixture comprising a phosphoromonochloridite represented by Formula II:

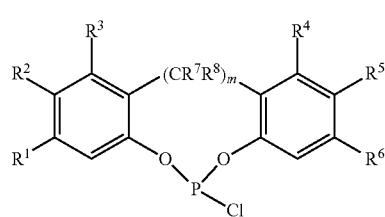

Formula II wherein m and $R^1$ through $R^8$ have the definitions given hereinabove, the second aromatic diol and excess phosphorous trichloride;
  (b) removing the excess phosphorous trichloride from the first mixture to obtain a second mixture comprising the phosphoromonochloridite and the second aromatic diol; and
  (c) adding a nitrogen base to the second mixture under conditions sufficient to react the second aromatic diol with the phosphoromonochloridite to produce a bisphosphite represented by Formula IV:

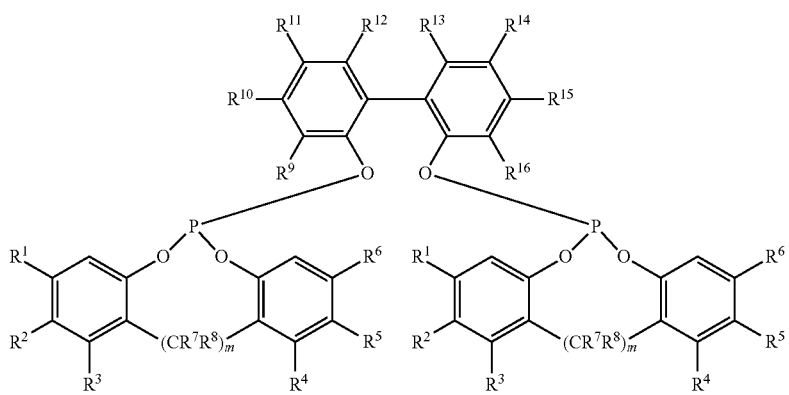

Formula IV wherein R¹ through R¹⁶ are as defined hereinabove.

DETAILED DESCRIPTION OF THE INVENTION

Certain phrases, terms, and words used in this Application are defined hereinafter. When interpreting a meaning of a phrase, term, or word, its definition here governs unless, for a particular use, a different meaning is stated elsewhere in this specification or unless a context of the use of the phrase, term, or word clearly indicates a different meaning is intended from the definitions provided herein.

The articles "a" and "the" refer to singular and plural forms of what is being modified by the articles. When used in front of a first member of a list of two or more members, the words "a" and "the" independently refer to each member in the list. As used herein, "a," "an," "the," "at least one," and "one or more" are used interchangeably. The term "comprises" and variations thereof do not have a limiting meaning where these terms appear in the description and claims. Thus, for example, a reactant mixture that comprises "an" aromatic diol can be interpreted to mean that the aromatic diol includes "one or more" aromatic diols.

All percentages, preferred amounts or measurements, ranges and endpoints thereof are inclusive, that is, "a range from 5 to 10" includes 5 and 10. "At least" is equivalent to "greater than or equal to," and "at most" is, thus, equivalent to "less than or equal to." Numbers herein have no more precision than stated. Thus, "115" includes at least from 114.6 to 115.4. All ranges from a parameter described as "at least," "greater than," "greater than or equal to" or similarly, to a parameter described as "at most," "up to," "less than," "less than or equal to" or similarly are preferred ranges regardless of the relative degree of preference indicated for each parameter. Thus a range that has an advantageous lower limit combined with a most preferred upper limit is preferred for the practice of this invention. The term "advantageously" is used to denote a degree of preference more than required, but less than is denoted by the term "preferably."

Except in the examples, or where otherwise indicated, all numbers expressing quantities, percentages, properties, functionalities and so forth in the specification are to be understood as being modified in all instances by the term "about." Unless stated otherwise, when an element, material, or step capable of causing undesirable effects is present in amounts or in a form such that it does not cause the effect to an unacceptable degree, that element, material, or step is considered substantially absent for the practice of this invention. Those skilled in the art recognize that acceptable limits vary with equipment, conditions, applications, and other variables, but are determinable without undue experimentation in each situation where they are applicable. In some instances, variation or deviation in one parameter is acceptable to achieve another desirable end.

As used herein, the phrase "having the formula" or "represented by the formula" is not intended to be limiting and is used in the same manner as the term "comprising" is commonly used.

The term "comprising," is synonymous with "including," "containing," or "characterized by," is inclusive or open-ended and does not exclude additional, unrecited elements, material, or steps. The term "consisting essentially of" indicates that in addition to specified elements, materials, or steps, unrecited elements, materials or steps are optionally present in amounts that do not unacceptably materially affect at least one basic and novel characteristic of the subject matter. The term "consisting of" indicates that only stated elements, materials or steps are present except that unrecited elements, materials or steps are optionally present to an extent that has no appreciable effect, or are substantially absent.

A "hydrocarbyl" moiety is defined as a monovalent moiety derived from a hydrocarbon by removal of one hydrogen atom from one carbon atom. A "hydrocarbon" shall have its ordinary meaning referring to a compound composed of carbon and hydrogen atoms. A hydrocarbyl can be an alkyl, alkenyl, alkynyl, or aryl, which is defined as a monovalent moiety derived from an alkane, alkene, alkyne, or arene, respectively, by removal of one hydrogen atom from one carbon atom. An alkyl can be a primary alkyl, secondary alkyl, or tertiary alkyl, which has two or three hydrogen atoms, one hydrogen atom, or no hydrogen atom, respectively; on the carbon atom that forms the alkyl.

A "hydrocarbylene" moiety is defined as a divalent moiety derived from a hydrocarbon by removal of two hydrogen atoms from two carbon atoms.

A "substituted hydrocarbyl" or "substituted hydrocarbylene" moiety means that one or more H or C atoms in the hydrocarbyl or the hydrocarbylene is substituted by one or more heteroatoms or one or more functional groups that contain one or more heteroatoms, which include, but are not limited to, nitrogen, oxygen, sulfur, phosphorus, boron, chlorine, bromine, and iodine. A substituted hydrocarbyl moiety can be a "hydrocarbyloxy" moiety, which has a generic formula of RO—, wherein R is a hydrocarbyl or substituted hydrocarbyl moiety as defined hereinabove.

The number of carbon atoms or a range thereof forming a moiety or compound is defined by prefixing the moiety or compound with a formula "$C_m$" or "$C_m$-$C_n$," respectively, wherein m and n are integers. For example, a $C_1$-$C_{10}$ hydrocarbyl means the hydrocarbyl has a number of carbon atoms in a range from one (1) to ten (10) carbon atoms.

Nomenclature of aromatic diols is illustrated by using the structure of 3,3'-di-tert-butyl-5,5'-dimethoxy-2,2'-biphenol below:

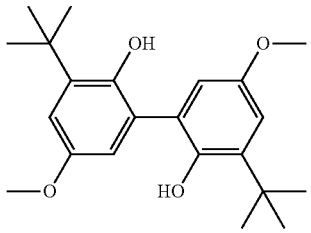

In the above structure, the carbon atoms that connect the two phenyl rings are assigned as 1 and 1' and the carbon atoms bearing the hydroxy groups are assigned as 2 and 2'. The carbon atoms connected to 2 and 2' carbons are assigned as 3, and 3', respectively, so on and so forth.

A "low hydrogen chloride solubility" in an organic solvent is defined as less than 0.2 moles of hydrogen chloride (HCl) per mole of solvent at a temperature of 20 degrees Celsius (° C.) and a total pressure of 760 millimeters of mercury (mm Hg) (101 kPa). The minimum hydrogen chloride solubility is not critical and may be effectively 0 moles of HCl per mole of solvent at a temperature of 20 degrees Celsius (° C.) and a total pressure of 760 millimeters of mercury (mm Hg) (101 kPa).

The term "organic solvent" has its ordinary meaning referring to an organic substance that is a liquid at ambient temperature and pressure and that is capable of dissolving another substance (solute) to form a uniformly dispersed mixture (solution) at a molecular or ionic level.

The term "ambient temperature" denotes a temperature of 22° C.±2° C.

The term "aprotic" refers herein to an organic solvent that does not donate protons.

Referring to an organic solvent, the term "boiling point" means the temperature at which the vapor pressure of the liquid phase equals a defined pressure of 1 atmosphere.

A "nitrogen base" is defined as a nitrogen-containing organic compound that is capable of neutralizing HCl to form a salt that is essentially insoluble in an organic solvent employed in the process. The nitrogen base preferably comprises no nitrogen-hydrogen bonds; more preferably, the nitrogen base comprises three alkyl substituents (trialkyl amine) or comprises a pyridine derivative (i.e., no hydrogen-nitrogen bonds).

Abbreviations and symbols "g," "hr," "L," "ml," "mol," "mmol," "NMR," "° C.," and "%" are used, respectively, for "gram," "hour" "liter," "milliliter," "mole," "millimole," "nuclear magnetic resonance," "degree Celsius," and "percent," respectively, and plural forms thereof. All pressures are expressed as absolute pressures.

Any reference to the Periodic Table of the Elements herein shall refer to the Periodic Table of the Elements published in *Nomenclature of Inorganic Chemistry: IUPAC Recommendations* 2005, Royal Society of Chemistry, 2005, ed. N. G. Connelly and T. Damhus. Also, any reference to a Group or Groups shall be to the Group or Groups reflected in this Periodic Table of the Elements using the IUPAC system for numbering groups.

The relevant teachings of each reference cited herein are incorporated to the maximum extent allowed by United States law. In the event of a conflict between a portion of an incorporated reference and this Application, this Application takes precedence over the incorporated portion.

As summarized hereinabove, in a first aspect, the present invention provides for a novel synthetic process for preparing a phosphoromonochloridite comprising contacting an aromatic diol (first aromatic diol) with phosphorus trichloride ($PCl_3$) in an organic solvent. The first aromatic diol employed in the invention is represented by Formula I:

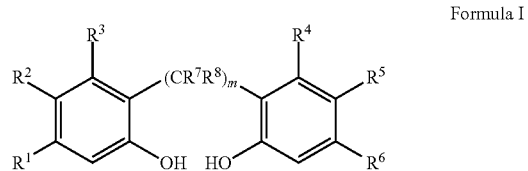

Formula I wherein m is zero, 1 or 2;
$R^1$, $R^2$, $R^3$, $R^4$, $R^5$, $R^6$, $R^7$ and $R^8$ are each independently selected from hydrogen, halogen, and $C_1$-$C_{10}$ substituted or unsubstituted hydrocarbyl moieties;
and wherein optionally, $R^2$ is bonded to $R^3$ to form a substituted or unsubstituted hydrocarbylene moiety so as to form a 5- or 6-membered ring; and/or
optionally, wherein $R^4$ is bonded to $R^5$ to form a substituted or unsubstituted hydrocarbylene moiety so as to form a 5- or 6-membered ring.

Preferably, m is zero or 1, and $R^7$ and $R^8$ are each hydrogen. More preferably, m is zero or 1, and $R^1$, $R^6$, $R^7$ and $R^8$ are each hydrogen. Compounds represented by Formula I are referred to herein as the "first aromatic diol," because in another preferred aspect of this invention as explained hereinafter, a second and different aromatic diol can also be employed in the process.

Examples of aromatic diols that can be employed as the first aromatic diol in the process include, but are not limited to 2,2'-biphenol, 5,5'-dimethyl-2,2'-biphenol, 5,5'-dichloro-2,2'-biphenol, 5,5'-dibromo-2,2'-biphenol, 5,5'-diiodo-2,2'-biphenol, 5,5'-diethyl-2,2'-biphenol, 5,5'-di-n-propyl-2,2'-biphenol, 5,5'-di-isopropyl-2,2'-biphenol, 5,5'-di-n-butyl-2,2'-biphenol, 5,5'-di-sec-butyl-2,2'-biphenol, 5,5'-di-iso-butyl-2,2'-biphenol, 5,5'-di-tert-butyl-2,2'-biphenol, 5,5'-di-n-amyl-2,2'-biphenol, 5,5'-bis(1,1-dimethylpropyl)-2,2'-biphenol, 5,5'-bis(2,2-dimethylpropyl)-2,2'-biphenol, 5,5'-di-n-hexyl-2,2'-biphenol, 5,5'-di-2-hexyl-2,2'-biphenol, 5,5'-di-3-hexyl-2,2'-biphenol, 5,5'-di-n-heptyl-2,2'-biphenol, 5,5'-di-2-heptyl-2,2'-biphenol, 5,5'-di-3-heptyl-2,2'-biphenol, 5,5'-di-4-heptyl-2,2'-biphenol, 5,5'-di-n-octyl-2,2'-biphenol, 5,5'-di-2-octyl-2,2'-biphenol, 5,5'-di-3-octyl-2,2'-biphenol, 5,5'-di-4-octyl-2,2'-biphenol, 5,5'-bis(1,1,3,3-tetramethylbutyl)-2,2'-biphenol, 5,5',6,6'-tetramethyl-2,2'-biphenol, 5,5'-diphenyl-2,2'-biphenol, 5,5'-bis(2,4,6,-trimethylphenyl)-2,2'-biphenol, 5,5'-dimethoxy-2,2'-biphenol, 5,5'-diethoxy-2,2'-biphenol, 5,5'-di-n-propoxy-2,2'-biphenol, 5,5'-di-isopropoxy-2,2'-biphenol, 5,5'-di-n-butoxy-2,2'-biphenol, 5,5'-di-sec-butoxy-2,2'-biphenol, 5,5'-di-iso-butoxy-2,2'-biphenol, 5,5'-di-tert-butoxy-2,2'-biphenol, 1,1'-bi-2-naphthol, bis(2-hydroxyphenyl)methane, 2,2'-methylenebis(4-chlorophenol), and 2,2'-methylenebis(4-tert-butyl-phenol). One preferred species of the aromatic diol is 2,2'-biphenol.

Phosphorus trichloride, as may be obtained from any commercial supplier, is also required for the process of this invention. The molar ratio of $PCl_3$ to the total amount of the first aromatic diol employed in the process advantageously is greater than 1.0, preferably greater than 1.1, and more preferably greater than 1.2; and advantageously is less than 3.5, preferably less than 3.3, more preferably less than 3.1, still more preferably less than 2.9, still more preferably less than 2.7, still more preferably less than 2.5, still more preferably less than 2.3, still more preferably less than 2.1, and still more preferably less than 1.9. As compared with the prior art, the aforementioned molar ratios of $PCl_3$ to total aromatic diol advantageously reduce the amount of excess unconverted $PCl_3$ to be removed upon completion of the condensation reaction.

While on one hand as seen above, a lower excess amount of $PCl_3$ to total aromatic diol is desirably employed; on the other hand, it is desirable to maintain a high molar ratio of $PCl_3$ to the dissolved first aromatic diol in the solution phase of the condensation reaction to minimize side reactions of the first aromatic diol with the phosphoromonochloridite reaction product. For example, 2,2'-biphenol can react with its reaction product, 1,1'-biphenyl-2,2'-diyl phosphoromonochloridite, to produce undesirable side products: 2'-(dibenzo[d,f][1,3,2]dioxaphosphepin-6-yloxy)biphenyl-2-ol (Formula V) and 2,2'-bis(dibenzo[d,f][1,3,2]dioxaphosphepin-6-yloxy)biphenyl (Formula VI).

Formula V

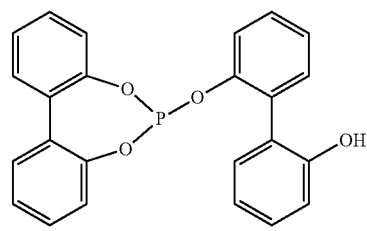

Formula VI

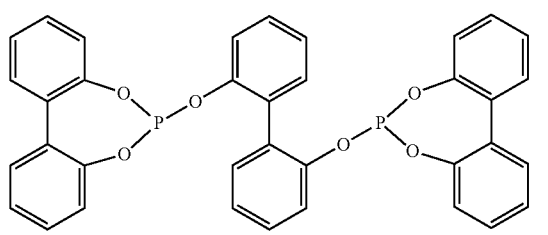

By selecting an organic solvent (and quantity thereof) that maintains a portion of the first aromatic diol in a slurry, i.e., partitioned between solid and solution phases, the process advantageously reaps the benefit of having a high molar ratio of $PCl_3$ to the dissolved first aromatic diol in the solution or reaction phase, while at the same time reaping the aforementioned benefit of having an overall lower excess amount of $PCl_3$ relative to total first aromatic diol.

Accordingly, desirable functions of the organic solvent in the process include, but are not limited to: a) reducing the concentration of the first aromatic diol in the solution phase to maintain a high molar ratio of $PCl_3$ to the dissolved first aromatic diol in the solution phase during the course of the condensation reaction, and b) facilitating the release of HCl from the condensation reaction solution. To perform at least one of the above described functions, the organic solvent for the process can be selected based on the following criteria: a) the solubility of the first aromatic diol in the organic solvent is greater than 1 percent, preferably greater than 2 percent, and more preferably greater than 3 percent, but less than 50 percent, by weight, based on the weight of the solution at 25° C.; and b) the solubility of HCl in the organic solvent is less than 0.2, preferably less than 0.1 mole of HCl per mole organic solvent at a temperature of 20° C. and a total pressure of 760 mm Hg (101 kPa).

The solubility of the first aromatic diol in the organic solvent can be measured by using known procedures. For example, the solubility of the first aromatic diol in the organic solvent at a specific temperature can be determined by an equilibrium solubility method, which employs a saturated solution of the first aromatic diol, obtained by stirring an excess amount of the first aromatic diol in the organic solvent at the specific temperature for a sufficient period of time until equilibrium is achieved. Thereafter, the resulting liquid phase saturated solution, the resulting solid phase, or both liquid and solid phases are analyzed by any conventional analytical method to arrive at the solubility of the first aromatic diol in the organic solvent.

Procedures for determining HCl solubility in an organic solvent are also well known. For example, bubbler procedures were used by Gerrard et al. (*Chem. Rev.,* 1959, 59, 1105) and Ahmed et al. (*J. Appl. Chem.,* 1970, Vol. 20, April, page 109-116.) for measuring HCl solubility in many organic solvents. Examples of HCl solubility in organic solvents reported by Gerrard et al. and Ahmed et al. are shown in Table 1.

TABLE 1

HCl Solubility in Organic Solvents at a total pressure of 760 mmHg (101 kPa)

| Organic solvent | HCl solubility Mol/mol organic solvent | |
|---|---|---|
| | At 10° C. | At 20° C. |
| n-Heptane | 0.02 | 0.015 |
| n-Decane | 0.028 | — |
| Benzene | 0.053 | 0.047 |
| Toluene | 0.07 | 0.051 |
| m-Xylene | 0.08 | 0.071 |
| o-Xylene | 0.08 | 0.061 |
| p-Xylene | 0.08 | 0.064 |
| Chlorobenzene | — | 0.033 |
| Tetrahydrofuran | 1.38 | — |
| Dioxane | 1.05 | — |
| Di-n-butyl ether | 0.89 | — |
| Dibenzyl ether | 0.54 | — |
| Methyl phenyl ether | 0.16 | — |
| Ethyl acetate | 0.66 | — |

Additional desirable functions of the organic solvent used in the process include, but are not limited to, a) keeping the phosphoromonochloridite of Formula II in the reaction solution; and b) simplifying isolation of the phosphoromonochloridite as a solution in the organic solvent by simplifying removal of any excess amount of $PCl_3$.

Advantageously, the organic solvent selected for the process has a boiling point greater than 90° C., preferably greater than 95° C., and more preferably greater than 100° C., but preferably less than 250° C., so that any excess $PCl_3$ used in the process can be preferentially removed from the reaction solution to obtain a product solution substantially comprising the phosphoromonochloridite and the organic solvent.

The organic solvent advantageously is selected from hydrocarbon solvents and chlorinated hydrocarbon solvents. Toluene, chlorobenzene, o-xylene, m-xylene, p-xylene, ethylbenzene, heptane, octane, and mixtures thereof are non-limiting examples of organic solvents that can be employed in the process. Dialkyl ethers, such as dibutyl ether, tetrahydrofuran (THF), and dioxane, are not used in the process due to the high solubility of HCl in such solvents (see Table 1); for example, a solubility greater than 0.2 mole HCl, preferably, greater than 0.5 mole HCl, per mole solvent at a temperature of 20° C. and a total pressure of 760 mm Hg (101 kPa) is not preferred for the organic solvent. As mentioned hereinbefore, under certain conditions, such as high temperatures, THF disadvantageously reacts with HCl to produce 4-chlorobutanol; see, for example, Barry et al., *Journal of Organic Chemistry* (1981), 46 (16), 3361-4. As an alcohol, 4-chlorobutanol is disadvantageously reactive towards the desired phosphoromonochloridite product.

The amount of the organic solvent to be employed in the process is determined in conjunction with the solubility of the first aromatic diol in the organic solvent. The amount of the organic solvent advantageously is such that greater than 1 percent, preferably greater than 3 percent, and more preferably greater than 5 percent, and advantageously less than 50 percent, preferably less than 40 percent, and more preferably less than 30 percent, by weight, of the total amount of the first aromatic diol is dissolved in the organic solvent. The balance of the first aromatic diol exists as a solid phase, thereby forming a slurry. The amount of the organic solvent in the slurry advantageously is greater than 20 percent, preferably greater than 25 percent, and more preferably greater than 30 percent, and advantageously is less than 95 percent, preferably less than 90 percent, and more preferably less than 85 percent, of the slurry by weight, based on the total weight of the slurry, which comprises the first aromatic diol in both solid and dissolved forms, $PCl_3$, and the organic solvent. Desirably, the amount of the organic solvent is sufficient to substantially solubilize the phosphoromonochloridite product after substantially all of the first aromatic diol is converted under reaction conditions. Advantageously, greater than 90 percent, preferably, greater than 95 percent, and essentially 100 percent, by weight, of the phosphoromonochloridite product is solubilized in the organic solvent. Typically, greater than 95 percent, preferably, greater than 98 percent, and more preferably, essentially 100 percent by weight of the total quantity of first aromatic diol is converted in the reaction.

Generally, the phosphoromonochloridite is more soluble than its starting aromatic diol in the organic solvent employed for the process, due to removal of hydrogen-bond-forming hydrogen atoms from the hydroxyl groups of the starting aromatic diol. The solubility of the phosphoromonochloridite in the selected organic solvent can be determined by an equilibrium solubility method as described above. Alternatively, the solubility of the phosphoromonochloridite in the selected organic solvent can be determined by producing the phosphoromonochloridite in a dilute solution of the organic solvent, for example, 1 percent by weight based on the weight of the dilute solution, and then evaporating the organic solvent from the dilute solution until a saturated solution of the phosphoromonochloridite is obtained. The concentration of the phosphoromonochloridite in the saturated solution can be determined by quantitative $^{31}P$ NMR or simple gravimetric analysis.

In one embodiment of the process, $PCl_3$ is initially contacted at ambient temperature with the slurry comprising the first aromatic diol in both solid and dissolved forms, the latter dissolved in the organic solvent. The temperature of the slurry is then raised advantageously in less than 2 hours, preferably less than 1.5 hours, but typically greater than 30 minutes, to a reaction temperature sufficient to produce the phosphoromonochloridite. The reaction temperature advantageously is greater than 25° C., preferably greater than 30° C., and advantageously is lower than 80° C., preferably lower than 75° C. The contacting advantageously is conducted at the reaction temperature for a reaction time sufficiently long that greater than 95 percent, preferably greater than 98 percent, and more preferably, essentially 100 percent of the first aromatic diol is converted in the reaction. The reaction time advantageously is greater than 3 hours, preferably greater than 6 hours, and advantageously is less than 48 hours, preferably less than 36 hours.

In another embodiment of the process, $PCl_3$ is initially contacted with the slurry at a temperature advantageously below 20° C., preferably below 15° C., more preferably below 10° C., still more preferably below 5° C., and still more preferably below 0° C. The minimum operable temperature lies above the freezing point of the selected organic solvent. Typically, the process is conducted at a temperature greater than −78° C. This range of lower initial contacting temperature prevents any unexpected rise in temperature due to the initial heat of mixing and reaction, which in turn may lead to unacceptably high initial reaction rates. Unacceptably high initial reaction rates disadvantageously may increase the extent to which side reactions occur between the first aromatic diol and its reaction product.

As the reaction progresses, the portion of the first aromatic diol in the solid form advantageously is dissolved over time to maintain a substantially constant concentration of the first aromatic diol in the solution phase. The solid first aromatic diol advantageously is substantially all dissolved when greater than 30 percent, preferably greater than 40 percent, and more preferably greater than 50 percent, of the first aromatic diol is converted in the reaction. After substantially all of the solid first aromatic diol is dissolved, the progress of the condensation reaction can be conveniently monitored by taking aliquots of the reaction solution for $^{31}P$ NMR analysis (disappearance of $PCl_3$ and appearance of the phosphoromonochloridite).

Contacting $PCl_3$ with the first aromatic diol in a slurry having a portion of the first aromatic diol in solid form reduces the concentration of the first aromatic diol in the solution phase, which reduces by-products formation between the first aromatic diol and its reaction product of Formulae II. By-products of Formulae V and VI, which are formed when the first aromatic diol is 2,2'-biphenol, can be reduced by the slurry method of this invention.

Generally, the process is carried out at ambient pressure, taken as 1 atmosphere (101 kPa); but higher or lower pressures may be employed, if desired. Preferably, the reaction is conducted under a blanket of inert atmosphere, such as nitrogen, argon, or helium. More preferably, a purge of inert atmosphere through the solution exiting the reactor to an HCl scrubber is used to aid in removing the liberated HCl.

The phosphoromonochloridite produced in the process advantageously is isolated as a solution of the organic solvent by removing excess $PCl_3$, either by evaporation under reduced pressures or by distillation under either atmospheric pressure or reduced pressures. Some of the organic solvent may be removed with the $PCl_3$ to ensure complete removal of $PCl_3$ or to obtain a solution having a preferred concentration of the phosphoromonochloridite. The removed $PCl_3$ and the removed organic solvent, if any, may be reused for a subsequent phosphoromonochloridite synthesis reaction to increase further the efficiency of the process. A neat phosphoromonochloridite product can be obtained by distillation, if desired. The yield of the phosphoromonochloridite advantageously is greater than 90 mole percent, and preferably, greater than 95 mole percent, based on the moles of total first aromatic diol employed in the process.

The yield of phosphoromonochloridite in the process can vary depending, at least partially, on levels of trace unidentified impurities in the first aromatic diol, which impurity levels vary with the source and/or specific batches of the first aromatic diol. It is desirable to obtain consistent yields of phosphoromonochloridite in the high end of the yield range. This has been surprisingly achieved by carrying out the condensation reaction in the presence of a trace amount of a base, preferably, a nitrogen base. Therefore, the process advantageously uses a trace amount of a base, preferably, a nitrogen base. The trace amount of nitrogen base advantageously is less than 5 mole percent, more preferably less than 3 mole percent, based on the total moles of the first aromatic diol used in the process. If a nitrogen base is used, then preferably, the trace amount of nitrogen base is greater than 0.01 mole percent, based on the total moles of the first aromatic diol used in the process. Non-limiting examples of nitrogen bases include pyridine, trialkylamine, and N,N-dialkylaniline, wherein any alkyl group is preferably C1-C15 alkyl. When the trace amount of base is employed, the yield of phosphoromonochloridite, preferably, the isolated yield, is advantageously greater than 93 mole percent, and more preferably greater than 96 mole percent, based on the total moles of first aromatic diol employed in the process.

In the prior art, when a nitrogen base is used to neutralize HCl in a phosphoromonochloridite synthesis process, as for example in, U.S. Pat. Nos. 5,235,113; 6,031,120, and 7,196,230, U.S patent application publication 2007/0112219 A1, and *Journal of Molecular Catalysis* A: Chemical 164 (2000) 125-130, the nitrogen base is generally used in an amount greater than one molar equivalent per molar equivalent of HCl produced. When employed in the present invention, the nitrogen base is not intended for neutralizing the HCl produced in the condensation reaction, because the trace amount of base used is less than 2.5 mole percent of the total moles of HCl produced in the process. If the trace amount of base neutralizes acid(s) present or produced in the condensation reaction, the resulting trace amount of salt(s) produce(s) no detrimental effect on the process and may, in fact, be carried with the phosphoromonochloridite in the organic solvent into a subsequent organopolyphosphite synthesis step.

The phosphoromonochloridite of Formula II, isolated from the process of this invention, is useful for preparing organopolyphosphites by condensing the phosphoromonochloridite with an organic poly-hydroxy compound in an organopolyphosphite synthesis reaction. Hydrogen chloride is produced as a co-product of this downstream process. The phosphoromonochloridite can be used either as a solution of the organic solvent or in neat form in the organopolyphosphite synthesis. The organopolyphosphite synthesis reaction advantageously is carried out in the presence of a nitrogen base in an amount sufficient to neutralize essentially all of the HCl produced. Isolation of the organopolyphosphite generally involves a procedure for removing the nitrogen base-HCl salt produced from neutralization either by filtration, or by aqueous workup; see, for example, U.S. Pat. Nos. 6,031,120; 5,663,369, and 4,769,498. It has been found that either salt-removing procedure for isolating the organopolyphosphite is effective in removing any trace amounts of salts carried over with the phosphoromonochloridite.

The process of the first aspect of the present invention described hereinabove has one or more of the following advantages, including: a) employing an organic solvent to reduce the concentration of the first aromatic diol in the solution phase of a slurry—thereby resulting in higher phosphoromonochloridite yield and less by-products; b) using a lower molar ratio of $PCl_3$ to the total first aromatic diol, as compared with the prior art, —thereby reducing excess amount of $PCl_3$; c) conducting the reaction at lower temperature without refluxing either a solvent or $PCl_3$—thereby simplifying operation and reducing energy need; d) producing little or no nitrogen base-HCl salt—thereby reducing waste and cost; and e) enabling recycle of recovered excess amount of $PCl_3$—thereby further improving efficiency and reducing cost.

In a second aspect, the present invention provides for a novel synthetic process for preparing a bisphosphite, which process comprises three steps as stated in the summary of the invention.

In the second aspect of the present invention, in step (a) a phosphoromonochloridite represented by Formula II hereinabove is produced by carrying out the process as described hereinbefore (i.e., in the first aspect of the present invention) in the presence of a second aromatic diol represented by Formula III:

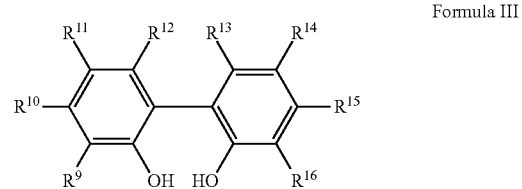

Formula III wherein:
$R^9$ and $R^{16}$ are each independently selected from $C_1$-$C_{10}$ substituted or unsubstituted hydrocarbyl moieties,
$R^{10}$ through $R^{15}$ are each independently selected from hydrogen, halogen, and $C_1$-$C_{10}$ substituted or unsubstituted hydrocarbyl moieties,
and wherein optionally, $R^{11}$ is bonded to $R^{12}$ to form a substituted or unsubstituted hydrocarbylene moiety so as to form a 5- or 6-membered ring; and/or
optionally, $R^{13}$ is bonded to $R^{14}$ to form a substituted or unsubstituted hydrocarbylene moiety so as to form a 5- or 6-membered ring;

Preferably, $R^9$ and $R^{16}$ are each independently selected from $C_1$-$C_{10}$ alkyl moieties. More preferably, $R^9$ and $R^{16}$ are each independently selected from $C_3$-$C_{10}$ secondary and tertiary alkyl moieties. Still more preferably, $R^9$ and $R^{16}$ are each independently selected from $C_4$-$C_{10}$ tertiary alkyl moieties. Still more preferably, $R^9$ and $R^{16}$ are each independently selected from $C_4$-$C_{10}$ tertiary alkyl moieties, $R^{10}$, $R^{12}$, $R^{13}$ and $R^{15}$ are each hydrogen, and $R^{11}$ and $R^{14}$ are each independently selected from $C_1$-$C_{10}$ substituted or unsubstituted alkyl moieties.

Examples of second aromatic diols that can be employed in the process include, but are not limited to 3,3',5,5'-tetramethyl-2,2'-biphenol, 3,3',5,5'-tetraethyl-2,2'-biphenol, 3,3',5, 5'-tetrapropyl-2,2'-biphenol, 3,3'-dimethyl-5,5'-dichloro-2, 2'-biphenol, 3,3'-diethyl-5,5'-dibromo-2,2'-biphenol, 3,3'-dimethyl-5,5'-diiodo-2,2'-biphenol, 3,3'-dimethyl-5,5'-diethyl-2,2'-biphenol, 3,3'-dimethyl-5,5'-di-n-propyl-2,2'-biphenol, 3,3',5,5'-tetra-isopropyl-2,2'-biphenol, 3,3',5,5'-tetra-sec-butyl-2,2'-biphenol, 3,3',5,5'-tetra-tert-butyl-2,2'-biphenol, 3,3'-di-tert-butyl-5,5'-di-n-amyl-2,2'-biphenol, 3,3',5,5'-tetrakis(1,1-dimethylpropyl)-2,2'-biphenol, 3,3'-di-tert-butyl-5,5'-bis(2,2-dimethylpropyl)-2,2'-biphenol, 3,3'-di-tert-butyl-5,5'-di-n-hexyl-2,2'-biphenol, 3,3'-di-tert-butyl-5,5'-di-2-hexyl-2,2'-biphenol, 3,3'-di-tert-butyl-5,5'-di-3-hexyl-2,2'-biphenol, 3,3'-di-tert-butyl-5,5'-di-n-heptyl-2,2'-biphenol, 3,3'-di-tert-butyl-5,5'-di-2-heptyl-2,2'-biphenol, 3,3'-di-tert-butyl-5,5'-di-3-heptyl-2,2'-biphenol, 3,3'-di-tert-butyl-5,5'-di-4-heptyl-2,2'-biphenol, 3,3'-di-tert-butyl-5,5'-di-n-octyl-2,2'-biphenol, 3,3'-di-tert-butyl-5,5'-di-2-octyl-2, 2'-biphenol, 5,5'-di-3-octyl-2,2'-biphenol, 3,3'-di-tert-butyl-5,5'-di-4-octyl-2,2'-biphenol, 3,3'-di-tert-butyl-5,5'-bis(1,1, 3,3-tetramethylbutyl)-2,2'-biphenol, 3,3',5,5'-tetrakis(1,1,3,3-tetramethylbutyl)-2,2'-biphenol, 3,3'-di-tert-butyl-5,5',6,6'-tetramethyl-2,2'-biphenol, 3,3'-di-tert-butyl-5,5'-diphenyl-2,2'-biphenol, 3,3'-di-tert-butyl-5,5'-bis(2,4,6,-trimethylphenyl)-2,2'-biphenol, 3,3'-di-tert-butyl-5,5'-dimethoxy-2,2'-biphenol, 3,3'-di-tert-butyl-5,5'-diethoxy-2,2'-biphenol, 3,3'-di-tert-butyl-5,5'-di-n-propoxy-2,2'-biphenol, 3,3'-di-tert-butyl-5,5'-di-isopropoxy-2,2'-biphenol, 3,3'-di-tert-butyl-5,5'-di-n-butoxy-2,2'-biphenol, 3,3'-di-tert-butyl-5,5'-di-sec-butoxy-2,2'-biphenol, 3,3'-di-tert-butyl-5,5'-di-iso-butoxy-2,2'-biphenol, 3,3'-di-tert-butyl-5,5'-di-tert-butoxy-2,2'-biphenol, and 3,3'-di-tert-butyl-1,1'-bi-2-naphthol. Preferred species of second aromatic diols are 3,3'-di-tert-butyl-5,5'-dimethoxy-2,2'-biphenol, 3,3',5,5'-tetra-tert-butyl-2,2'-biphenol (iso-BHT-diol), and 3,3',5,5'-tetrakis(1,1-dimethylpropyl)-2,2'-biphenol.

The second aromatic diol is employed in an amount sufficient to consume in subsequent process steps substantially all of the phosphoromonochloridite produced from the first aromatic diol. The amount of second aromatic diol is preferably more than 35 mole percent, and more preferably, more than 40 mole percent, based on the moles of the first aromatic diol employed. The amount of second aromatic diol is preferably less than 50 mole percent, more preferably less than 45 mole percent, based on the moles of the first aromatic diol employed.

The second aromatic diol is advantageously at least partially soluble in the organic solvent employed. Preferably, more than 5 percent, more preferably more than 10 percent by weight of the second aromatic diol is dissolved in the organic solvent. It is also possible that the second aromatic diol is only partially dissolved at the beginning of this step (a) of the process, but is completely dissolved during or at completion of this step.

It is noted that the second aromatic diol is required to be substantially non-reactive under the process conditions of step (a), which means that less than 5 weight percent, preferably, less than 3 weight percent, and preferably, less than 1 weight percent of the second aromatic diol is converted under the operating conditions of step (a) to a condensation product with $PCl_3$. As a useful guideline, the skilled person can evaluate the reactivity of the second aromatic diol in a separate test reaction that excludes the first aromatic diol and base. Such evaluation is conducted under at least the reaction conditions of step (a), although a higher temperature than that intended for step (a) can be used. More specifically, a lab-scale quantity (e.g., 5-10 grams) of the second aromatic diol can be charged into a nitrogen-purged flask equipped with nitrogen inlet and vent line. Degassed organic solvent of choice (e.g., 30-75 ml) is added; the mixture is cooled to 0° C., and then $PCl_3$ is added in stoichiometric excess. The resulting slurry is heated under a flow of the inert atmosphere at the desired reaction temperature for step (a), or a higher temperature, for at least 12 hours, preferably, 1 day, up to about 3 days. Then, the slurry is filtered; and the recovered solids and filtrate are analyzed separately by $^{31}P$ NMR for the presence of any condensation product between the $PCl_3$ and the second aromatic diol. As a specific example, when 3,3'5,5'-tetra-tert-butyl-2,2'-biphenol is heated under nitrogen in toluene for 3 days at 80° C., which is higher than the preferred operating temperature of step (a), it was observed that less than 2 percent of the 3,3'5,5'-tetra-tert-butyl-2,2'-biphenol reacts to form condensation product. Accordingly, any second aromatic diol exhibiting the aforementioned lack of reactivity in step (a) can be suitably employed in this process. From another perspective, the second aromatic diol functions essentially as a spectator until step (c) is reached.

Other reaction conditions for carrying out step (a) of the second aspect of the present invention are essentially the same as the reactions conditions described hereinbefore for the process of the first aspect of the present invention. The process conditions are sufficient to react the first aromatic diol with the $PCl_3$ to produce a phosphoromonochloridite represented by Formula II hereinabove. The second aromatic diol, on the other hand, remains essentially unreacted, even when $PCl_3$ is used in molar excess of the first aromatic diol. Therefore, under the reaction conditions of step (a), a first mixture is obtained that comprises the phosphoromonochloridite, the second aromatic diol, and excess $PCl_3$.

In step (b) in the second aspect of the present invention, the excess $PCl_3$ in the first mixture is removed by carrying out a procedure similar to the phosphoromonochloridite isolation procedure described hereinbefore to obtain a second mixture comprising the phosphoromonochloridite and the second aromatic diol. Similar to the phosphoromonochloridite isolation procedure described hereinbefore, some of the organic solvent may be removed with the $PCl_3$ to ensure complete removal of $PCl_3$. The removed $PCl_3$ and the removed organic solvent, if any, may be reused for a subsequent phosphoromonochloridite synthesis reaction to increase the efficiency of the process. An additional amount of the organic solvent can be added to the second mixture to make up any organic solvent removed during removal of the excess $PCl_3$.

In step (c) of the process in the second aspect of the present invention, a nitrogen base is added into the second mixture. The added nitrogen base promotes a reaction between the second aromatic diol and the phosphoromonochloridite, which will be referred to as bisphosphite formation reaction hereinafter, to produce a bisphosphite represented by Formula IV:

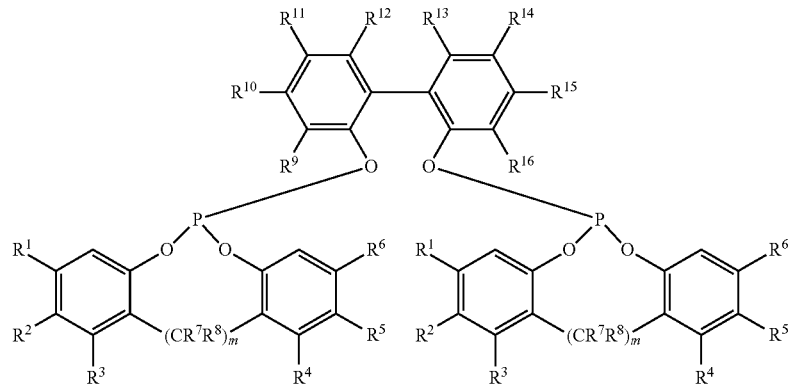

Formula IV wherein m and $R^1$ through $R^{16}$ are as defined hereinabove.

Any nitrogen base known in the art to be effective in carrying out the bisphosphite formation reaction can be employed, for example those disclosed in U.S. Pat. Nos. 6,031,120, 5,663,369, and 4,769,498. Polymeric amines can also be used in carry out the bisphosphite formation reaction. Preferred nitrogen bases are trialkylamines and pyridines. Non-limiting examples of suitable nitrogen bases are triethylamine, tripropylamine, N,N-diisopropylethylamine, and pyridine. If trace amount of a nitrogen base is used in step (a), the same nitrogen base can be used in this step (c), although a different nitrogen base can be used if desired.

The nitrogen base is employed in an amount sufficient to provide a molar ratio of the nitrogen base to the second aromatic diol of advantageously at least 2.0:1, preferably at least 2.1:1, more preferably at least 2.2:1, and advantageously less than 3.0:1, preferably less than 2.9:1, and more preferably less than 2.8:1.

Preferably, the second mixture is cooled to a temperature of 15° C. or lower, more preferably 0° C. or lower. The temperature is preferably greater than −78° C., and more preferably greater than −30° C. The nitrogen base is then added into the cooled second mixture over a period of advantageously greater than 15 minutes, preferably greater than 30 minutes, and advantageously less than 2 hours and preferably less than 1 hour. The reaction mixture is then allowed to warm to ambient temperature and stirred at ambient temperature for an additional period of time sufficiently long to react at least 90 percent, preferably at least 95 percent, and more preferably at least 98 percent of the second aromatic diol with the phosphoromonochloridite to obtain a final reaction solution comprising the bisphosphite represented by Formula IV. The additional period of time is preferably at least 1 hour, more preferably at least 2 hours, and is preferably less than 36 hours and preferably less than 24 hours. Progress of the bisphosphite formation reaction can be conveniently monitored by taking aliquots of the reaction solution for $^{31}$P NMR analysis (disappearance of phosphoromonochloridite and appearance of the bisphosphite). In case an insufficient amount of the second aromatic diol is employed at the beginning of the process, as determined by $^{31}$P NMR analysis, an additional amount of the second aromatic diol can be added at this time to essentially completely consume all the phosphoromonochloridite in the second mixture.

The bisphosphite product can be isolated and purified by procedures known in the art, for examples those disclosed in U.S. Pat. No. 4,769,498. Water, for example, can be added to the final reaction solution followed by phase separation to remove salts produced in the process and to obtain an organic solution. The organic solution can be optionally dried by any known means, for example, by using a drying agent or by azeotropical distillation. Any known drying agent can be used so long as the drying agent does not unduly absorb or react with the bisphosphite. Examples of suitable drying agents include sodium chloride, sodium sulfate, magnesium sulfate and molecular sieves. The bisphosphite is usually isolated by crystallization by concentrating the organic solution and/or cooling the organic solution. Recrystallization of the isolated bisphosphite can be carried out, if necessary or desired, to further purify the bisphosphite. The yield of isolated bisphosphite, calculated based on the moles of the second aromatic diol, is advantageously greater than 75 mole percent, and preferably, greater than 80 mole percent.

The process of the second aspect of the present invention described hereinabove has one or more of the same advantages as the process of the first aspect of the present invention. By adding the second aromatic diol with the first aromatic diol into the reactor as a solid at the beginning, the process of the second aspect of the present invention has the following additional one or more advantages, including: a) eliminating any need of dissolving the second aromatic diol in a tank or another reactor; b) reducing the amount of the organic solvent; c) eliminating the need of handling an organic solution of the second aromatic diol; and d) employing only one step wherein solids handling equipment is required. When the bisphosphite is produced according to the prior art via synthesis of the phosphoromonochloridite in a first reactor followed by synthesis of the bisphosphite in a second reactor, both reactors and their connecting pipes and conduits need to be purged with an inert atmosphere ("inerting") to avoid flammable conditions and reduce solvent fumes. Conducting the synthesis of the bisphosphite in one reactor in accordance with this invention advantageously reduces inerting to only one reactor with consequential shorter cycle times between runs.

SPECIFIC EMBODIMENTS OF THE INVENTION

The following examples are illustrative of the present invention and are not to be regarded as limiting thereof. Variations in reaction conditions, such as reactants, temperatures and solvents, will be apparent to those skilled in the art, based on the description and examples contained herein. All parts, percentages, and proportions referred to herein are given by weight, unless otherwise indicated. Regarding $^{31}$P NMR analyses, the spectrometer is standardized by setting phosphoric acid to δ=0.0 ppm.

Example 1

Preparation of 1,1'-biphenyl-2,2'-diyl phosphoromonochloridite 2,2'-Biphenol (6.2 g, 33 mmol) is charged into a nitrogen purged, dry 250 ml, 3-necked round-bottom flask equipped with a septum port, a magnetic stir bar, and a reflux condenser, which is topped with a nitrogen inlet and a vent line to a scrubber. Degassed anhydrous toluene (50 ml, 43 g) is added and the resulting slurry is cooled with an ice bath to 0° C., followed by addition of $PCl_3$ (7.1 g, 51 mmol) and then pyridine (0.1 ml, 1 mmol). The resulting slurry, which contains solid 2,2'-biphenol, dissolved 2,2'-biphenol, $PCl_3$ and toluene, is stirred while being warmed to 35° C. over a period of 60 minutes and then stirred at 35° C. overnight, during which time the solid dissolves to give a clear solution. $^{31}$P NMR analysis shows only surplus $PCl_3$ and 1,1'-biphenyl-2,2'-diyl phosphoromonochloridite (δ=180.5 ppm) with less than 5 mole percent impurities. The solution is distilled up to 94° C. to remove excess $PCl_3$ (bp=76°).

Example 2

Preparation of 6,6'-(3,3',5,5'-tetra-tert-butylbiphenyl-2,2'-diyl)bis(oxy)didibenzo[d,f][1,3,2]-dioxaphosphepine Powders of 2,2'-biphenol (6.25 g, 0.0335 moles) and 3,3',5,5'-tetra-tert-butyl-2,2'-biphenol (iso-BHT-diol, 6.80 g, 0.0166 moles) are charged into a nitrogen-purged, dry, 250 ml, 3-necked round-bottom flask, equipped with a nitrogen inlet and a vent line to a scrubber, a septum port, and a magnetic stir bar. The powders are degassed and then toluene (50 ml) is added to obtain a slurry. The slurry is cooled to ice temperature (0° C.). Phosphorous trichloride ($PCl_3$, 7.1 g, 0.051 moles) is added into the cooled slurry, followed by addition of pyridine (0.1 ml (0.001 mole). The resulting slurry is stirred while warming to ambient temperature over a period of 60 minutes then stirred overnight at 35° C., over which time the solids are dissolved to give a clear light yellow solution. $^{31}$P NMR analysis shows only excess PCl$_3$ and phosphoromonochloridite (δ=180.5 ppm) with less than 10% other impurities. (The iso-BHT-diol will not be detected since it lacks a P atom.) The solution is distilled up to 136° C. to remove the excess PCl$_3$ (bp=76°) to obtain a solution containing the phosphoromonochloridite and the iso-BHT-diol. After cooling the solution to ice temperature (0° C.), 25 ml toluene is added and then 8.0 g pyridine (0.1 mole) diluted in 25 ml toluene is added dropwise over a period of 45 minutes, resulting in a mixture containing a tan solid. The mixture is stirred overnight, during which the temperature rises to ambient temperature. $^{31}$P NMR analysis of the supernatant of the mixture shows very clean conversion of the phosphoromonochloridite and the iso-BHT-diol to the desired bisphosphite, 6,6'-(3,3',5,5'-tetra-tert-butylbiphenyl-2,2'-diyl)bis(oxy)didibenzo[d,f][1,3,2]dioxaphosphepine (δ=146.0 ppm) with less than 10% total impurities.

Embodiments of the Invention

The following embodiments of the invention are envisioned:

1. A process for preparing a phosphoromonochloridite comprising contacting phosphorus trichloride (PCl$_3$) with an aromatic diol represented by the formula:

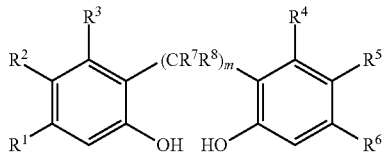

wherein:
  m is zero, 1 or 2;
  $R^1$, $R^2$, $R^3$, $R^4$, $R^5$, $R^6$, $R^7$ and $R^8$ are each independently selected from hydrogen, halogen, and $C_1$-$C_{10}$ substituted or unsubstituted hydrocarbyl moieties;
  and wherein optionally, $R^2$ is bonded to $R^3$ to form a substituted or unsubstituted hydrocarbylene moiety so as to form a 5- or 6-membered ring; and/or
  optionally, $R^4$ is bonded to $R^5$ to form a substituted or unsubstituted hydrocarbylene moiety so as to form a 5- or 6-membered ring, in a slurry comprising a portion of the aromatic diol in solid form and comprising a solution phase comprising the remaining portion of the aromatic diol and an organic solvent, wherein the slurry comprises less than 5 mole percent of a nitrogen base calculated on total moles of the aromatic diol, and the organic solvent has a low hydrogen chloride solubility; the contacting being conducted under reaction conditions sufficient to produce a phosphoromonochloridite represented by the formula:

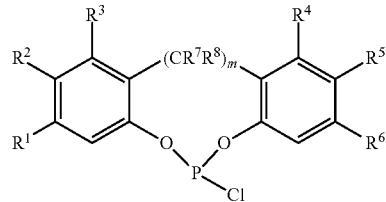

wherein m and $R^1$ through $R^8$ have the definitions given hereinabove.

2. The aforementioned embodiment, wherein m is zero or 1.

3. Any one of the aforementioned embodiments, wherein $R^1$, $R^6$, $R^7$ and $R^8$ are each hydrogen.

4. Any one of the aforementioned embodiments, wherein the aromatic diol is selected from, but not limited to, the following: 2,2'-biphenol, 5,5'-dimethyl-2,2'-biphenol, 5,5'-dichloro-2,2'-biphenol, 5,5'-dibromo-2,2'-biphenol, 5,5'-di-iodo-2,2'-biphenol, 5,5'-diethyl-2,2'-biphenol, 5,5'-di-n-propyl-2,2'-biphenol, 5,5'-di-isopropyl-2,2'-biphenol, 5,5'-di-n-butyl-2,2'-biphenol, 5,5'-di-sec-butyl-2,2'-biphenol, 5,5'-di-iso-butyl-2,2'-biphenol, 5,5'-di-tert-butyl-2,2'-biphenol, 5,5'-di-n-amyl-2,2'-biphenol, 5,5'-bis(1,1-dimethylpropyl)-2,2'-biphenol, 5,5'-bis(2,2-dimethylpropyl)-2,2'-biphenol, 5,5'-di-n-hexyl-2,2'-biphenol, 5,5'-di-2-hexyl-2,2'-biphenol, 5,5'-di-3-hexyl-2,2'-biphenol, 5,5'-di-n-heptyl-2,2'-biphenol, 5,5'-di-2-heptyl-2,2'-biphenol, 5,5'-di-3-heptyl-2,2'-biphenol, 5,5'-di-4-heptyl-2,2'-biphenol, 5,5'-di-n-octyl-2,2'-biphenol, 5,5'-di-2-octyl-2,2'-biphenol, 5,5'-di-3-octyl-2,2'-biphenol, 5,5'-di-4-octyl-2,2'-biphenol, 5,5'-bis(1,1,3,3-tetramethylbutyl)-2,2'-biphenol, 5,5',6,6'-tetramethyl-2,2'-biphenol, 5,5'-diphenyl-2,2'-biphenol, 5,5'-bis(2,4,6,-trimethylphenyl)-2,2'-biphenol, 5,5'-dimethoxy-2,2'-biphenol, 5,5'-diethoxy-2,2'-biphenol, 5,5'-di-n-propoxy-2,2'-biphenol, 5,5'-di-isopropoxy-2,2'-biphenol, 5,5'-di-n-butoxy-2,2'-biphenol, 5,5'-di-sec-butoxy-2,2'-biphenol, 5,5'-di-iso-butoxy-2,2'-biphenol, 5,5'-di-tert-butoxy-2,2'-biphenol, 1,1'-bi-2-naphthol, bis(2-hydroxyphenyl)methane, 2,2'-methylenebis(4-chlorophenol), and 2,2'-methylenebis(4-cert-butyl-phenol), preferably, 2,2'-biphenol.

5. Any one of the aforementioned embodiments, wherein the organic solvent has a hydrogen chloride (HCl) solubility of less than 0.2 mole, preferably less than 0.1 mole of HCl per mole organic solvent, measured at a temperature of 20° C. and a total pressure of 760 mm Hg (101 kPa).

6. Any one of the aforementioned embodiments, wherein the organic solvent has a boiling point greater than 90° C., preferably greater than 95° C., and more preferably greater than 100° C., but preferably less than 250° C.

7. Any one of the aforementioned embodiments, wherein the organic solvent is selected from the group consisting of toluene, chlorobenzene, o-xylene, m-xylene, p-xylene, ethylbenzene, heptane, octane, and mixtures thereof.

8. Any one of the aforementioned embodiments, wherein the organic solvent is used in an amount of from greater than 20 percent, preferably greater than 25 percent, and more preferably, greater than 30 percent, and less than 95 percent, preferably less than 90 percent, and more preferably less than 85 percent by weight, based on the total weight of the slurry.

9. Any one of the aforementioned embodiments, wherein the molar ratio of the PCl$_3$ to the aromatic diol is advantageously greater than 1.0, preferably greater than 1.1, and more preferably greater than 1.2; and advantageously is less than 3.5, preferably less than 3.3, more preferably less than 3.1, still more preferably less than 2.9, still more preferably less than 2.7, still more preferably less than 2.5, still more preferably less than 2.3, still more preferably less than 2.1, and still more preferably less than 1.9.

10. Any one of the aforementioned embodiments, wherein the process comprises contacting PCl$_3$ with the aromatic diol at a reaction temperature advantageously greater than 25° C., preferably greater than 30° C., and advantageously lower than 80° C., preferably lower than 75° C.

11. Any one of the aforementioned embodiments, wherein the process is conducted out at ambient pressure, taken as 1 atmosphere (101 kPa); but higher or lower pressures may be employed, if desired; preferably, the process is conducted under a blanket of inert atmosphere, such as nitrogen, argon, or helium.

12. Any one of the aforementioned embodiments, wherein the reaction time advantageously is greater than 3 hours, preferably greater than 6 hours, and advantageously is less than 48 hours, preferably less than 36 hours.

13. Any one of the aforementioned embodiments, wherein PCl$_3$ is initially contacted with the slurry at a temperature advantageously below 20° C., preferably below 15° C., more preferably below 10° C., still more preferably below 5° C., and still more preferably below 0° C., but greater than the freezing point of the selected organic solvent, preferably greater than −78° C.

14. Any one of the aforementioned embodiments, wherein the contacting is conducted in the presence of a nitrogen base in an amount less than 5 mole percent, more preferably less than 3 mole percent; but if the base is used, then in an amount greater than 0.01 mole percent, based on the total moles of the aromatic diol used in the process.

15. Any one of the aforementioned embodiments, wherein the nitrogen base is selected from the group consisting of pyridine, trialkylamine, and N,N-dialkylaniline, wherein any alkyl group is preferably C1-C15 alkyl.

16. Any one of the aforementioned embodiments, wherein the process further comprises removing unreacted PCl$_3$ to obtain a product solution comprising the phosphoromonochloridite and the organic solvent.

17. Any one of the aforementioned embodiments, wherein all or a portion of the unreacted PCl$_3$ is recovered and recycled to the process.

18. A process for preparing 1,1'-biphenyl-2,2'-diyl phosphoromonochloridite, the process comprising contacting PCl$_3$ with 2,2'-biphenol in a slurry, which slurry comprises a portion of the 2,2'-biphenol in solid form and comprises a solution phase comprising the remaining portion of the 2,2'-biphenol and an organic solvent, at a reaction temperature greater than 25° to less than 75° C. for a time sufficient to convert greater than 95 mole percent of the 2,2'-biphenol to 1,1'-biphenyl-2,2'-diylphosphoromonochloridite; wherein the slurry comprises less than 5 mole percent of a nitrogen base, calculated on total moles of 2,2'-biphenol, the molar ratio of the PCl$_3$ to 2,2'-biphenol is greater than 1.0/1 to less than 3.5/1, and the organic solvent has a hydrogen chloride solubility of less than 0.2 mole HCl per mole organic solvent measured at a temperature of 20° C. and a total pressure of 760 mm Hg (101 kPa).

19. A process for preparing a bisphosphite, the process comprising the steps of:

(a) contacting phosphorus trichloride with a first aromatic diol represented by the formula:

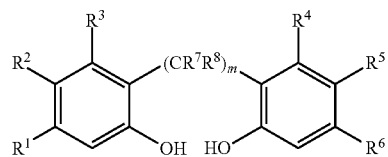

wherein:
m is zero, 1 or 2;
R$^1$, R$^2$, R$^3$, R$^4$, R$^5$, R$^6$, R$^7$ and R$^8$ are each independently selected from hydrogen, halogen, and C$_1$-C$_{10}$ substituted or unsubstituted hydrocarbyl moieties;
and wherein optionally, R$^2$ is bonded to R$^3$ to form a substituted or unsubstituted hydrocarbylene moiety so as to form a 5- or 6-membered ring; and/or
optionally, R$^4$ is bonded to R$^5$ to form a substituted or unsubstituted hydrocarbylene moiety so as to form a 5- or 6-membered ring,
in the presence of a second aromatic diol represented by the formula:

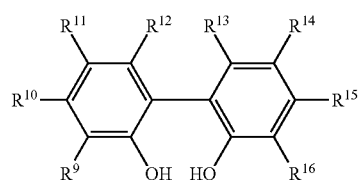

wherein:
R$^9$ and R$^{16}$ are each independently selected from C$_1$-C$_{10}$ substituted or unsubstituted hydrocarbyl moieties,
R$^{10}$ through R$^{15}$ are each independently selected from hydrogen, halogen, and C$_1$-C$_{10}$ substituted or unsubstituted hydrocarbyl moieties,
and wherein optionally, R$^{11}$ is bonded to R$^{12}$ to form a substituted or unsubstituted hydrocarbylene moiety so as to form a 5- or 6-membered ring;
and/or optionally, R$^{13}$ is bonded to R$^{14}$ to form a substituted or unsubstituted hydrocarbylene moiety so as to form a 5- or 6-membered ring;
the contacting being conducted in a slurry comprising portions of both first and second aromatic diols in solid forms and comprising a solution phase comprising the remaining portions of both first and second aromatic diols and an organic solvent, wherein the slurry comprises less than 5 mole percent of a nitrogen base, calculated on total moles of the first aromatic diol, and the organic solvent has a low hydrogen chloride solubility; the contacting being conducted under reaction conditions sufficient to produce a first mixture comprising a phosphoromonochloridite represented by the formula:

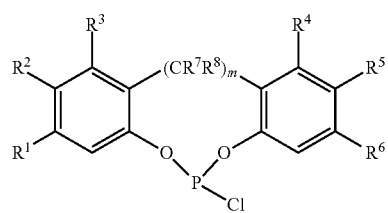

wherein m and $R^1$ through $R^8$ have the definitions given hereinabove, the second aromatic diol and excess phosphorous trichloride;

(b) removing the excess phosphorous trichloride from the first mixture to obtain a second mixture comprising the phosphoromonochloridite and the second aromatic diol; and (c) adding a nitrogen base to the second mixture under conditions sufficient to react the second aromatic diol with the phosphoromonochloridite to produce a bisphosphite represented by the formula:

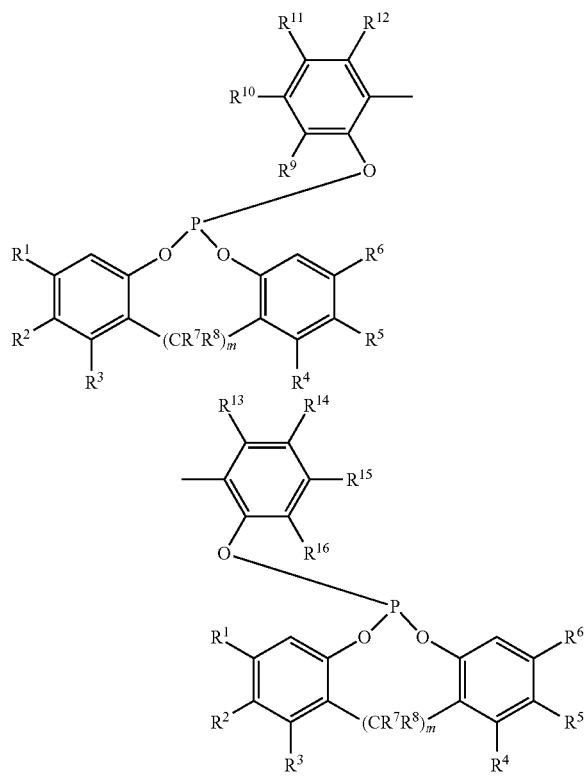

wherein m and $R^1$ through $R^{16}$ are as defined hereinabove.

20. The embodiment of 19, wherein m is zero or 1.

21. Any one of embodiments 19 or 20, wherein $R^1$, $R^6$, $R^7$ and $R^8$ are each hydrogen.

22. Any one of embodiments 19 to 21, wherein the first aromatic diol is 2,2'-biphenol.

23. Any one of embodiments 19 to 22, wherein $R^9$ and $R^{16}$ are each independently selected from $C_1$-$C_{10}$ alkyl moieties.

24. Any one of embodiments 19 to 22, wherein $R^9$ and $R^{16}$ are each independently selected from $C_3$-$C_{10}$ secondary alkyl moieties.

25. Any one of embodiments 19 to 22, wherein $R^9$ and $R^{16}$ are each independently selected from $C_4$-$C_{10}$ tertiary alkyl moieties.

26. Any one of embodiments 19 to 22, wherein $R^9$ and $R^{16}$ are each independently selected from $C_4$-$C_{10}$ tertiary alkyl moieties, $R^{10}$, $R^{12}$, $R^{13}$ and $R^{15}$ are hydrogen, and $R^{11}$ and $R^{14}$ are each independently selected from $C_1$-$C_{10}$ substituted or unsubstituted alkyl moieties.

27. Any one of embodiments 19 to 26, wherein the second aromatic diol is selected from 3,3',5,5'-tetramethyl-2,2'-biphenol, 3,3',5,5'-tetraethyl-2,2'-biphenol, 3,3',5,5'-tetrapropyl-2,2'-biphenol, 3,3'-dimethyl-5,5'-dichloro-2,2'-biphenol, 3,3'-diethyl-5,5'-dibromo-2,2'-biphenol, 3,3'-dimethyl-5,5'-diiodo-2,2'-biphenol, 3,3'-dimethyl-5,5'-diethyl-2,2'-biphenol, 3,3'-dimethyl-5,5'-di-n-propyl-2,2'-biphenol, 3,3',5,5'-tetra-isopropyl-2,2'-biphenol, 3,3',5,5'-tetra-sec-butyl-2,2'-biphenol, 3,3',5,5'-tetra-tert-butyl-2,2'-biphenol, 3,3'-di-tert-butyl-5,5'-di-n-amyl-2,2'-biphenol, 3,3',5,5'-tetrakis(1,1-dimethylpropyl)-2,2'-biphenol, 3,3'-di-tert-butyl-5,5'-bis(2,2-dimethylpropyl)-2,2'-biphenol, 3,3'-di-tert-butyl-5,5'-di-n-hexyl-2,2'-biphenol, 3,3'-di-tert-butyl-5,5'-di-2-hexyl-2,2'-biphenol, 3,3'-di-tert-butyl-5,5'-di-3-hexyl-2,2'-biphenol, 3,3'-di-tert-butyl-5,5'-di-n-heptyl-2,2'-biphenol, 3,3'-di-tert-butyl-5,5'-di-2-heptyl-2,2'-biphenol, 3,3'-di-tert-butyl-5,5'-di-3-heptyl-2,2'-biphenol, 3,3'-di-tert-butyl-5,5'-di-4-heptyl-2,2'-biphenol, 3,3'-di-tert-butyl-5,5'-di-n-octyl-2,2'-biphenol, 3,3'-di-tert-butyl-5,5'-di-2-octyl-2,2'-biphenol, 5,5'-di-3-octyl-2,2'-biphenol, 3,3'-di-tert-butyl-5,5'-di-4-octyl-2,2'-biphenol, 3,3'-di-tert-butyl-5,5'-bis(1,1,3,3-tetramethylbutyl)-2,2'-biphenol, 3,3',5,5'-tetrakis(1,1,3,3-tetramethylbutyl)-2,2'-biphenol, 3,3'-di-tert-butyl-5,5',6,6'-tetramethyl-2,2'-biphenol, 3,3'-di-tert-butyl-5,5'-diphenyl-2,2'-biphenol, 3,3'-di-tert-butyl-5,5'-bis(2,4,6,-trimethylphenyl)-2,2'-biphenol, 3,3'-di-tert-butyl-5,5'-dimethoxy-2,2'-biphenol, 3,3'-di-tert-butyl-5,5'-diethoxy-2,2'-biphenol, 3,3'-di-tert-butyl-5,5'-di-n-propoxy-2,2'-biphenol, 3,3'-di-tert-butyl-5,5'-di-isopropoxy-2,2'-biphenol, 3,3'-di-tert-butyl-5,5'-di-n-butoxy-2,2'-biphenol, 3,3'-di-tert-butyl-5,5'-di-sec-butoxy-2,2'-biphenol, 3,3'-di-tert-butyl-5,5'-di-iso-butoxy-2,2'-biphenol, 3,3'-di-tert-butyl-5,5'-di-tert-butoxy-2,2'-biphenol, and 3,3'-di-tert-butyl-1,1'-bi-2-naphthol. Preferred species of second aromatic diols are 3,3'-di-tert-butyl-5,5'-dimethoxy-2,2'-biphenol, 3,3',5,5'-tetra-cert-butyl-2,2'-biphenol (iso-BHT-diol), and 3,3',5,5'-tetrakis(1,1-dimethylpropyl)-2,2'-biphenol.

28. Any one of embodiments 19 to 27, wherein the organic solvent has a hydrogen chloride (HCl) solubility of less than 0.2 mole, preferably less than 0.1 mole of HCl per mole organic solvent, measured at a temperature of 20° C. and a total pressure of 760 mm Hg (101 kPa).

29. Any one of embodiments 19 to 28, wherein the organic solvent has a boiling point greater than 90° C., preferably greater than 95° C., and more preferably greater than 100° C., but preferably less than 250° C.

30. Any one of embodiments 19 to 29, wherein the organic solvent is selected from the group consisting of toluene, chlorobenzene, o-xylene, m-xylene, p-xylene, ethylbenzene, heptane, octane, and mixtures thereof.

31. Any one of embodiments 19 to 30, wherein the organic solvent is used in an amount of from greater than 20 percent to less than 95 percent of the slurry by weight, based on the weight of the slurry.

32. Any one of embodiments 19 to 31, wherein the molar ratio of the $PCl_3$ to the first aromatic diol is advantageously greater than 1.0, preferably greater than 1.1, and more preferably greater than 1.2; and advantageously is less than 3.5, preferably less than 3.3, more preferably less than 3.1, still more preferably less than 2.9, still more preferably less than 2.7, still more preferably less than 2.5, still more preferably less than 2.3, still more preferably less than 2.1, and still more preferably less than 1.9.

33. Any one of embodiments 19 to 32, wherein the contacting of step (a) is conducted at a reaction temperature advantageously greater than 25° C., preferably greater than 30° C., and advantageously lower than 80° C., preferably lower than 75° C.

34. Any one of embodiments 19 to 33, wherein the reaction time of step (a) is from greater than 3 hours to less than 48 hours such that greater than 95 mole percent of the first aromatic diol is converted in the reaction.

35. Any one of embodiments 19 to 34, wherein step (a) of the process further comprises contacting PCl₃ with the first aromatic diol at an initial temperature in a range from greater than −78° C. to below 20° C., which is then raised to the reaction temperature from greater than 25° to less than 80° C.

36. Any one of embodiments 19 to 35, wherein the contacting of step (a) is conducted in the presence of a nitrogen base in an amount less than 5 mole percent, more preferably less than 3 mole percent; but if the base is used, then in an amount greater than 0.01 mole percent, based on the total moles of the aromatic diol used in the process.

37. The embodiment 36, wherein the nitrogen base is selected from the group consisting of pyridine, trialkylamine, and N,N-dialkylaniline, wherein any alkyl group is preferably a C1-C15 alkyl.

38. Any one of embodiments 19 to 37, wherein the nitrogen base added into the second mixture in step (c) is in an amount sufficient to provide a molar ratio of the nitrogen base to the second aromatic diol of advantageously at least 2.0:1, preferably at least 2.1:1, more preferably at least 2.2:1, and advantageously less than 3.0:1, preferably less than 2.9:1, and more preferably less than 2.8:1

39. The embodiment 38, wherein the nitrogen base is added into the second mixture at a temperature of 15° C. or lower, more preferably 0° C. or lower; but preferably greater than −78° C., and more preferably greater than −30° C.

40. A process for preparing 6,6'-(3,3',5,5'-tetra-tert-butyl-biphenyl-2,2'-diyl)bis(oxy)didibenzo[d,f][1,3,2]dioxaphosphepine, the process comprising the steps of:

(a) contacting PCl₃ with 2,2'-biphenol in the presence of 3,3',5,5'-tetra-tert-butyl-2,2'-biphenol in a slurry, which slurry comprises portions of the 2,2'-biphenol and 3,3',5,5'-tetra-tert-butyl-2,2'-biphenol in solid forms and comprises a solution phase comprising the remaining portions of the 2,2'-biphenol and 3,3',5,5'-tetra-tert-butyl2,2'-biphenol in an organic solvent, at a reaction temperature greater than 25° to less than 75° C. for a time sufficient to convert greater than 95 mole percent of the 2,2'-biphenol to 1,1'-biphenyl-2,2'-diyl phosphoromonochloridite; wherein the slurry comprises less than 5 mole percent of a nitrogen base, calculated on total moles of 2,2'-biphenol, the molar ratio of the PCl₃ to 2,2'-biphenol is greater than 1.0/1 to less than 3.5/1, and the organic solvent has a hydrogen chloride solubility of less than 0.2 mole HCl per mole organic solvent measured at a temperature of 20° C. and a total pressure of 760 mm Hg (101 kPa); whereby obtaining a first mixture comprising 1,1'-biphenyl-2,2'-diyl phosphoromonochloridite, 3,3',5,5'-tetra-tert-butyl-2,2'-biphenol and excess PCl₃;

(b) removing the excess PCl₃ to obtain a second mixture comprising 1,1'-biphenyl-2,2'-diyl phosphoromonochloridite and 3,3',5,5'-tetra-tert-butyl-2,2'-biphenol; and (c) adding a nitrogen base selected from the group consisting of trialkylamine and pyridine in an amount sufficient to provide a molar ratio of the nitrogen base to 3,3',5,5'-tetra-tert-butyl-2,2'-biphenol of at least 2.0 and less than 3.0, under conditions sufficient to produce 6,6'-(3,3',5,5'-tetra-tert-butylbiphenyl-2,2'-diyl)bis(oxy)didibenzo[d,f][1,3,2]dioxaphosphepine.

41. A reaction composition comprising phosphorus trichloride, a first aromatic diol represented by the formula:

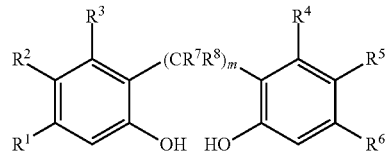

wherein:
m is zero, 1 or 2;
$R^1$, $R^2$, $R^3$, $R^4$, $R^5$, $R^6$, $R^7$ and $R^8$ are each independently selected from hydrogen, halogen, and $C_1$-$C_{10}$ substituted or unsubstituted hydrocarbyl moieties;
and wherein optionally, $R^2$ is bonded to $R^3$ to form a substituted or unsubstituted hydrocarbylene moiety so as to form a 5- or 6-membered ring; and/or
optionally, $R^4$ is bonded to $R^5$ to form a substituted or unsubstituted hydrocarbylene moiety so as to form a 5- or 6-membered ring;
and a second aromatic diol represented by the formula:

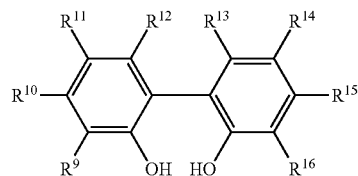

wherein:
$R^9$ and $R^{16}$ are each independently selected from $C_1$-$C_{10}$ substituted or unsubstituted hydrocarbyl moieties,
$R^{10}$ through $R^{15}$ are each independently selected from hydrogen, halogen, and $C_1$-$C_{10}$ substituted or unsubstituted hydrocarbyl moieties,
and wherein optionally, $R^{11}$ is bonded to $R^{12}$ to form a substituted or unsubstituted hydrocarbylene moiety so as to form a 5- or 6-membered ring;
and/or optionally, $R^{13}$ is bonded to $R^{14}$ to form a substituted or unsubstituted hydrocarbylene moiety so as to form a 5- or 6-membered ring.

42. Embodiment 42 further comprising an organic solvent such that the composition comprises a slurry in which portions of the first and second aromatic diols are in solid phases and the remaining portions of the first and second aromatic diols are dissolved in the organic solvent to form a solution phase.

What is claimed is:
1. A process for preparing a bisphosphite, the process comprising the steps of:
(a) contacting phosphorus trichloride with a first aromatic diol represented by the formula:

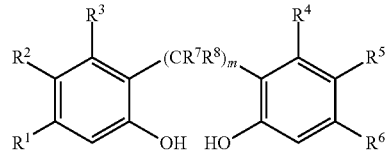

wherein:
m is zero, 1 or 2;
$R^1$, $R^2$, $R^3$, $R^4$, $R^5$, $R^6$, $R^7$ and $R^8$ are each independently selected from the group consisting of hydrogen, halogen, and $C_1$-$C_{10}$ substituted or unsubstituted hydrocarbyl moieties;
and wherein optionally, $R^2$ is bonded to $R^3$ to form a substituted or unsubstituted hydrocarbylene moiety so as to form a 5- or 6-membered ring; and/or
optionally, $R^4$ is bonded to $R^5$ to form a substituted or unsubstituted hydrocarbylene moiety so as to form a 5- or 6-membered ring,
in the presence of a second aromatic diol represented by the formula:

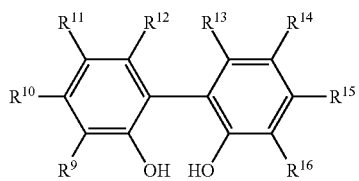

wherein:
$R^9$ and $R^{16}$ are each independently selected from $C_1$-$C_{10}$ substituted or unsubstituted hydrocarbyl moieties,
$R^{10}$ through $R^{15}$ are each independently selected from the group consisting of hydrogen, halogen, and $C_1$-$C_{10}$ substituted or unsubstituted hydrocarbyl moieties,
and wherein optionally, $R^{11}$ is bonded to $R^{12}$ to form a substituted or unsubstituted hydrocarbylene moiety so as to form a 5- or 6-membered ring;
and/or optionally, $R^{13}$ is bonded to $R^{14}$ to form a substituted or unsubstituted hydrocarbylene moiety so as to form a 5- or 6-membered ring;
the contacting being conducted in a slurry comprising portions of both first and second aromatic diols in solid forms and comprising a solution phase comprising the remaining portions of both first and second aromatic diols and an organic solvent, wherein the slurry comprises less than 5 mole percent of a nitrogen base, calculated on total moles of the first aromatic diol, and the organic solvent has a low hydrogen chloride solubility; the contacting being conducted under reaction conditions sufficient to produce a first mixture comprising a phosphoromonochloridite represented by the formula:

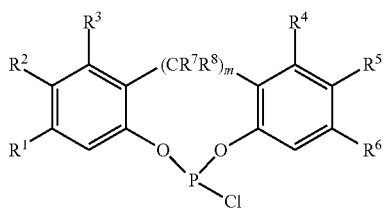

wherein m and $R^1$ through $R^8$ have the definitions given hereinabove, the second aromatic diol and excess phosphorous trichloride;
(b) removing the excess phosphorous trichloride from the first mixture to obtain a second mixture comprising the phosphoromonochloridite and the second aromatic diol; and
(c) adding a nitrogen base to the second mixture under conditions sufficient to react the second aromatic diol with the phosphoromonochloridite to produce a bisphosphite represented by the formula:

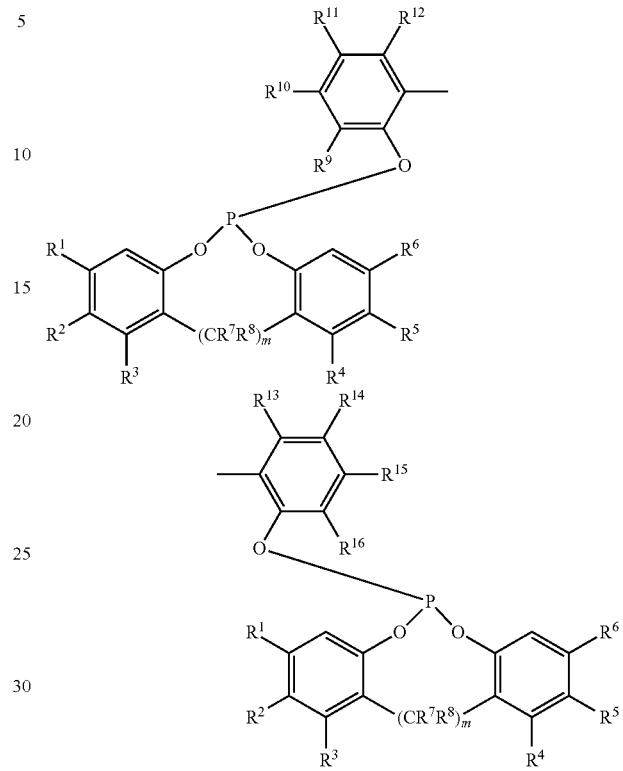

wherein m and $R^1$ through $R^{16}$ are as defined hereinabove.

2. The process of claim 1, wherein m is zero or 1 and wherein $R^1$, $R^6$, $R^7$ and $R^8$ are each hydrogen.

3. The process of claim 1, wherein $R^9$ and $R^{16}$ are each independently selected from $C_4$-$C_{10}$ tertiary alkyl moieties.

4. The process of claim 1, wherein $R^9$ and $R^{16}$ are each independently selected from $C_4$-$C_{10}$ tertiary alkyl moieties, $R^{10}$, $R^{12}$, $R^{13}$ and $R^{15}$ are hydrogen, and $R^{11}$ and $R^{14}$ are each independently selected from $C_1$-$C_{10}$ substituted or unsubstituted alkyl moieties.

5. The process of claim 1, wherein the second aromatic diol is selected from 3,3'-di-tert-butyl-5,5'-dimethoxy-2,2'-biphenol, 3,3',5,5'-tetra-tert-butyl-2,2'-biphenol and 3,3',5,5'-tetrakis(1,1-dimethylpropyl)-2,2'-biphenol.

6. The process of claim 1, wherein the organic solvent has a hydrogen chloride (HCl) solubility of less than 0.2 mole HCl per mole organic solvent, measured at a temperature of 20° C. and a total pressure of 760 mm Hg (101 kPa) and wherein the organic solvent has a normal boiling point of greater than 90° C. and less than 250° C.

7. The process of claim 1, wherein the contacting of step (a) is conducted at a reaction temperature from greater than 25° to less than 80° C.

8. The process of claim 1, wherein the contacting of step (a) is conducted in the presence of a nitrogen base in an amount from greater than 0.01 mole percent to less than 5 mole percent, calculated on total moles of the first aromatic diol.

9. The process of claim 1, wherein the nitrogen base added into the second mixture in step (c) is in an amount sufficient to provide a molar ratio of the nitrogen base to the second aromatic diol of at least 2.0 and less than 3.0.

10. A process for preparing 6,6'-(3,3',5,5'-tetra-tert-butyl-biphenyl-2,2'-diyl)bis(oxy)didibenzo[d,f][1,3,2]dioxaphosphepine, the process comprising the steps of:

(a) contacting PCl$_3$ with 2,2'-biphenol in the presence of 3,3',5,5'-tetra-tert-butyl-2,2'-biphenol in a slurry, which slurry comprises portions of the 2,2'-biphenol and 3,3',5,5'-tetra-tert-butyl-2,2'-biphenol in solid forms and comprises a solution phase comprising the remaining portions of the 2,2'-biphenol and 3,3',5,5'-tetra-tert-butyl-2,2'-biphenol in an organic solvent, at a reaction temperature greater than 25° to less than 75° C. for a time sufficient to convert greater than 95 mole percent of the 2,2'-biphenol to 1,1'-biphenyl-2,2'-diyl phosporomonochloridite; wherein the slurry comprises less than 5 mole percent of a nitrogen base, calculated on total moles of 2,2'-biphenol, the molar ratio of the PCl$_3$ to 2,2'-biphenol is greater than 1.0/1 to less than 3.5/1, and the organic solvent has a hydrogen chloride solubility of less than 0.2 mole HCl per mole organic solvent measured at a temperature of 20° C. and a total pressure of 760 mm Hg (101 kPa); whereby obtaining a first mixture comprising 1,1'-biphenyl-2,2'-diyl phosporomonochloridite, 3,3',5,5'-tetra-tert-butyl-2,2'-biphenol and excess PCl$_3$;

(b) removing the excess PCl$_3$ to obtain a second mixture comprising 1,1'-biphenyl-2,2'-diyl phosporomonochloridite and 3,3',5,5'-tetra-tert-butyl-2,2'-biphenol; and (c) adding a nitrogen base selected from the group consisting of trialkylamine and pyridine in an amount sufficient to provide a molar ratio of the nitrogen base to 3,3',5,5'-tetra-tert-butyl-2,2'-biphenol of at least 2.0 and less than 3.0, under conditions sufficient to produce 6,6'-(3,3',5,5'-tetra-tert-butylbiphenyl-2,2'-diyl)bis(oxy)didibenzo[d,f][1,3,2]dioxaphosphepine.

\* \* \* \* \*